(12) United States Patent
Hall et al.

(10) Patent No.: US 11,517,879 B2
(45) Date of Patent: *Dec. 6, 2022

(54) **CHROMATOGRAPHY LIGAND COMPRISING DOMAIN C FROM *STAPHYLOCOCCUS AUREUS* PROTEIN A FOR ANTIBODY ISOLATION**

(71) Applicant: Cytiva Bioprocess R&D AB, Uppsala (SE)

(72) Inventors: Martin Hall, Uppsala (SE); Sture Larsson, Uppsala (SE); Andreas Muranyi, Uppsala (SE); Gustav Rodrigo, Uppsala (SE); Jinyu Zou, Uppsala (SE); Per-Mikael Aberg, Uppsala (SE)

(73) Assignee: CYTIVA BIOPROCESS R&D AB, Uppsala (SE)

( * ) Notice: Subject to any disclaimer, the term of this patent is extended or adjusted under 35 U.S.C. 154(b) by 0 days.

This patent is subject to a terminal disclaimer.

(21) Appl. No.: 17/107,600

(22) Filed: Nov. 30, 2020

(65) Prior Publication Data

US 2021/0291143 A1 Sep. 23, 2021

Related U.S. Application Data

(60) Continuation of application No. 16/443,600, filed on Jun. 17, 2019, now Pat. No. 10,875,007, which is a continuation of application No. 16/189,894, filed on Nov. 13, 2018, now Pat. No. 10,343,142, which is a continuation of application No. 15/603,285, filed on May 23, 2017, now Pat. No. 10,213,765, which is a continuation of application No. 15/063,471, filed on Mar. 7, 2016, now Pat. No. 9,663,559, which is a division of application No. 14/164,519, filed on Jan. 27, 2014, now Pat. No. 9,290,549, which is a continuation-in-part of application No. 13/559,663, filed on Jul. 27, 2012, now Pat. No. 8,772,447, which is a division of application No. 12/443,011, filed as application No. PCT/SE2007/000862 on Sep. 27, 2007, now Pat. No. 8,329,860.

(30) Foreign Application Priority Data

Sep. 29, 2006 (SE) .................................. 0602061-4

(51) Int. Cl.
| | |
|---|---|
| *B01J 20/24* | (2006.01) |
| *B01D 15/38* | (2006.01) |
| *B01J 20/286* | (2006.01) |
| *C07K 1/22* | (2006.01) |
| *B01J 20/32* | (2006.01) |
| *C07K 14/31* | (2006.01) |
| *C07K 16/00* | (2006.01) |
| *C07K 17/00* | (2006.01) |
| *B01J 20/28* | (2006.01) |
| *B01J 20/285* | (2006.01) |
| *B01J 20/289* | (2006.01) |
| *C07K 17/10* | (2006.01) |

(52) U.S. Cl.
CPC .......... *B01J 20/24* (2013.01); *B01D 15/3809* (2013.01); *B01J 20/285* (2013.01); *B01J 20/286* (2013.01); *B01J 20/289* (2013.01); *B01J 20/28019* (2013.01); *B01J 20/3212* (2013.01); *B01J 20/3219* (2013.01); *B01J 20/3274* (2013.01); *B01J 20/3293* (2013.01); *C07K 1/22* (2013.01); *C07K 14/31* (2013.01); *C07K 16/00* (2013.01); *C07K 17/00* (2013.01); *C07K 17/10* (2013.01); *B01J 2220/52* (2013.01); *B01J 2220/54* (2013.01); *C07K 2317/55* (2013.01)

(58) Field of Classification Search
None
See application file for complete search history.

(56) References Cited

U.S. PATENT DOCUMENTS

| | | |
|---|---|---|
| 5,084,559 A | 1/1992 | Profy |
| 5,151,350 A | 9/1992 | Colbert et al. |
| 5,260,373 A | 11/1993 | Profy et al. |
| 6,399,750 B1 | 6/2002 | Johansson |
| 6,831,161 B1 | 12/2004 | Uhlén et al. |

(Continued)

FOREIGN PATENT DOCUMENTS

| | | |
|---|---|---|
| EP | 0550771 A1 | 7/1993 |
| EP | 1992692 B1 | 1/2013 |

(Continued)

OTHER PUBLICATIONS

Arshady, R et al., "Styrene Based Polymer Supports Developed by Suspension Polymerization", La Chimica El'Industria, 70(9):70-75 (1988).

Bowie et al., "Deciphering the message in protein sequences: tolerance to amino acid substitutions" (Science, 1990, N7:1306-1310).

(Continued)

*Primary Examiner* — Brian Gangle
(74) *Attorney, Agent, or Firm* — Culhane Meadows, PLLC; Jeff B. Vockrodt

(57) ABSTRACT

The present invention relates to a chromatography ligand, which comprises Domain C from *Staphylococcus* protein A (SpA), or a functional fragment or variant thereof. The chromatography ligand presents an advantageous capability of withstanding harsh cleaning in place (CIF) conditions, and is capable of binding Fab fragments of antibodies. The ligand may be provided with a terminal coupling group, such as arginine or cysteine, to facilitate its coupling to an insoluble carrier such as beads or a membrane. The invention also relates process of using the ligand in isolation of antibodies, and to a purification protocol which may include washing steps and/or regeneration with alkali.

14 Claims, 2 Drawing Sheets

Specification includes a Sequence Listing.

(56) References Cited

U.S. PATENT DOCUMENTS

| | | | |
|---|---|---|---|
| 8,329,860 | B2 | 12/2012 | Hall et al. |
| 8,728,828 | B2 | 5/2014 | Berg |
| 8,772,447 | B2 | 7/2014 | Hall et al. |
| 9,290,549 | B2 | 3/2016 | Hall et al. |
| 9,663,559 | B2 | 5/2017 | Hall et al. |
| 10,213,765 | B2 | 2/2019 | Hall et al. |
| 10,343,142 | B2 | 7/2019 | Hall et al. |
| 2005/0100970 | A1 | 5/2005 | Uhlen et al. |
| 2006/0134805 | A1 | 6/2006 | Berg |
| 2006/0194950 | A1 | 8/2006 | Hober et al. |
| 2006/0194955 | A1 | 8/2006 | Hober et al. |

FOREIGN PATENT DOCUMENTS

| | | |
|---|---|---|
| EP | 2066419 B1 | 11/2015 |
| JP | 20060304633 A | 11/2006 |
| WO | 93002107 A1 | 2/1993 |
| WO | 00069457 A1 | 11/2000 |
| WO | 03080655 A1 | 10/2003 |
| WO | 2006065208 A1 | 6/2006 |
| WO | 2006092338 A2 | 9/2006 |
| WO | 2008039141 A1 | 4/2008 |

OTHER PUBLICATIONS

Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", The Journal of Cell Biology, Nov. 1990, vol. 111, pp. 2129-2138.

Gulich, S. et al., "Stability towards alkaline conditions can be engineered into a protein ligand" Journal of Biotechnology, 80 (2000), pp. 169-178.

Hermanson et al., "Immobilized Affinity Ligand Techniques", Academic Press (1992), p. 118.

Hjerten, S., "The Preparation of Agarose Spheres for Chromatography of Molecules and Particles", Biochimica et Biophysica Acta, 79 (1964) pp. 393-398.

Hober, S. et al., "Protein A chromatography for antibody purification", Journal of Chromatography B, 848 (2007) pp. 40-47.

International Preliminary Report on Patentability received for PCT Patent Application No. PCT/SE2007/000862, dated Mar. 31, 2009 (10 pages).

International Search Report and Written Opinion issued in International Patent Application No. PCT/SE2007/000862, dated Jan. 28, 2008 (16 pages).

Jansson, B. et al., "All individual domains of Staphylococcal protein A show Fab binding," FEMS Immunology and Medical Microbiology, 20, (1998), pp. 69-78.

Lazar et al., "Transforming Growth Factor beta: Mutation of Aspartic Acid 47 and Leucine 48 Results in Different Biological Activities", Molecular and Cellular Biology, 1988, vol. 8, pp. 1247-1252.

Minakuchi et al., "Remarkable alkaline stability of an engagement of an engineered protein A as immunoglobulin affinity ligand: C domain having only amino acid substitution," Protein Science, 22 (2013), pp. 1230-1238.

Nilsson et al., "A synthetic IgG-binding domain based on staphylococcal protein A," Protein Engineering, vol. 1 (2), 1987, pp. 107-113.

Office Action corresponding to European Patent Application No. 07808849.9, dated Feb. 18, 2014, 7 pages.

Office Action corresponding to European Patent Application No. 07808849.9, dated Sep. 16, 2014, 7 pages.

Office Action received in Chinese Application No. 201610565445.3 dated Sep. 13, 2021, with translation, 15 pages.

Rongxiu, et al., "Enzyme Engineering in Pharmaceuticals," Chemical Industry Press, May 2004, with translation, 6 pages.

Shigen, et al., "Enzymology," Fudan University Press, Feb. 2001, with translation, 6 pages.

SEQUENCE LISTING

```
<160> NUMBER OF SEQ ID NOS: 2

<210> SEQ ID NO 1
<211> LENGTH: 58
<212> TYPE: PRT
<213> ORGANISM: Staphylococcus aureus

<400> SEQUENCE: 1

Ala Asp Asn Lys Phe Asn Lys Glu Gln Gln Asn Ala Phe Tyr Glu Ile
1               5                   10                  15

Leu His Leu Pro Asn Leu Thr Glu Glu Gln Arg Asn Gly Phe Ile Gln
            20                  25                  30

Ser Leu Lys Asp Asp Pro Ser Val Ser Lys Glu Ile Leu Ala Glu Ala
        35                  40                  45

Lys Lys Leu Asn Asp Ala Gln Ala Pro Lys
    50                  55

<210> SEQ ID NO 2
<211> LENGTH: 54
<212> TYPE: PRT
<213> ORGANISM: Staphylococcus aureus

<400> SEQUENCE: 2

Ala Asp Lys Glu Gln Gln Asn Ala Phe Tyr Glu Ile Leu His Leu Pro
1               5                   10                  15

Asn Leu Thr Glu Glu Gln Arg Asn Gly Phe Ile Gln Ser Leu Lys Asp
            20                  25                  30

Asp Pro Ser Val Ser Lys Glu Ile Leu Ala Glu Ala Lys Lys Leu Asn
        35                  40                  45

Asp Ala Gln Ala Pro Lys
    50
```

CHROMATOGRAPHY LIGAND COMPRISING DOMAIN C FROM *STAPHYLOCOCCUS AUREUS* PROTEIN A FOR ANTIBODY ISOLATION

CROSS-REFERENCE TO RELATED APPLICATIONS

This application is a continuation of U.S. patent application Ser. No. 16/189,894, filed Nov. 13, 2018, which is a continuation of U.S. patent application Ser. No. 15/603,285, filed on May 23, 2017, which is a continuation of U.S. patent application Ser. No. 15/063,471, filed on Mar. 7, 2016, now U.S. Pat. No. 9,663,559, which is a division of U.S. patent application Ser. No. 14/164,519, filed Jan. 27, 2014, now U.S. Pat. No. 9,290,549, which is a continuation of U.S. patent application Ser. No. 13/559,663, filed Jul. 27, 2012, now U.S. Pat. No. 8,772,447, which is a division of U.S. patent application Ser. No. 12/443,011 filed on Mar. 26, 2009, and now U.S. Pat. No. 8,329,860, which This application is a filing under 35 U.S.C. § 371 and claims priority to international patent application number PCT/SE2007/000862 filed Sep. 27, 2007, published on Apr. 3, 2008, as WO 2008/039141, which claims priority to patent application number 0602061-4 filed in Sweden on Sep. 29, 2006, the entire disclosures of each of which are hereby incorporated by reference.

STATEMENT REGARDING SEQUENCE LISTING

The Sequence Listing associated with this application is part of the description and is provided in text the form of an Annex C/ST.25 text file in lieu of the text file containing the Sequence Listing is 220662-19 PU06101 CON DIV1 CON_Sequence Listing.txt. The text file is 2 kb, was created on May 23, 2017, and is being submitted herewith electronically via EFS-Web.

FIELD OF THE INVENTION

The present invention relates to the field of chromatography, and more specifically to a novel affinity ligand which is suitable for use in antibody isolation. Thus, the invention encompasses affinity ligands as such, a chromatography matrix comprising ligands according to the invention, and a process of antibody isolation, wherein the ligand according to the invention is used.

BACKGROUND OF THE INVENTION

The term chromatography embraces a family of closely related separation methods based on the contacting of two mutually immiscible phases, wherein one phase is stationary and the other phase is mobile. One area wherein chromatography is of great interest is in the biotechnological field, such as for large-scale economic production of drugs and diagnostics. Generally, proteins are produced by cell culture, either intracellularly or by secretion into the surrounding medium. Since the cell lines used are living organisms, they must be fed with a complex growth medium containing sugars, amino acids, growth factors, etc. Separation of the desired protein from the mixture of compounds fed to the cells and from other cellular components to a sufficient purity, e.g. for use as a human therapeutic, poses a formidable challenge.

In such separation, in a first step, cells and/or cell debris is usually removed by filtration. Once a clarified solution containing the protein of interest has been obtained, its separation from the other components of the solution is often performed using a combination of different chromatography steps, often based on different separation principles. Thus, such steps separate proteins from mixtures on the basis of charge, degree of hydrophobicity, affinity properties, size etc. Several different chromatography matrices, such as matrices for ion exchange, hydrophobic interaction chromatography (HIC), reverse phase chromatography (RPC), affinity chromatography and immobilized metal affinity chromatography (IMAC), are available for each of these techniques, allowing tailoring of the purification scheme to the particular protein involved. An illustrative protein, which is of steadily growing interest in the medical field, is immunoglobulin proteins, also known as antibodies, such as immunoglobulin G (IgG).

As in all process technology, an important aim is to keep the production costs low. Consequently, improved chromatographic techniques are frequently presented, and the matrices are when possible reused. However, since each use of a chromatography matrix will leave certain traces of the operation just performed, many different cleaning protocols are available for cleaning and/or restoring the matrix into its original form. Commonly known materials that need to be removed are e.g. non-eluted proteins and protein aggregates as well as potentially hazardous materials, such as virus, endotoxins etc, which may originate from the cell culture. The most commonly used cleaning is a simple wash with buffer. For a more efficient cleaning of the matrix, treatments with acid and/or base are frequently used. In order to even more efficiently restore the matrix, an alkaline protocol known as Cleaning In Place (CIP) is commonly used. The standard CIP involves treatment of the matrix with 1M NaOH, pH 14. Such harsh treatment will efficiently remove undesired fouling of the above-discussed kind, but may in addition impair some chromatography matrix materials. For example, many affinity matrices, wherein the ligands are proteins or protein-based, cannot withstand standard CIP, at least not while maintaining their original properties. It is known that structural modification, such as deamidation and cleavage of the peptide backbone, of asparagine and glutamine residues in alkaline conditions is the main reason for loss of activity upon treatment of protein in alkaline solutions, and that asparagine is the most sensitive of the two. It is also known that the deamidation rate is highly specific and conformation dependent, and that the shortest deamidation half times in proteins have been associated with the sequences—asparagine-glycine- and -asparagine-serine. See e.g. Gülich, Linhult, Nygren, Uhlen and Hober (2000) Journal of Biotechnology 80, 169-178. Stability towards alkaline conditions can be engineered into a protein ligand.

Despite the documented alkaline sensitivity, protein A is widely used as a ligand in affinity chromatography matrices due to its ability to bind IgG without significantly, affecting the affinity of immunoglobulin for antigen. As is well known, Protein A is a constituent of the cell wall of the bacterium *Staphylococcus aureus*. Such *Staphylococcus* protein, known as SpA, is composed of five domains, designated in order from the N-terminus as E, D, A, B, and C, which are able to bind antibodies at the Fc region, and a C-terminal region (or "X" region) that does not bind any antibodies. Jansson et al (Jansson, Uhlen and Nygren (1998) FEMS Immunology and Medical Microbiology 20, 69-78: "All individual domains of staphylococcal protein A show Fab binding") have later shown that all the individual SpA domains also bind certain antibodies at the Fab region.

U.S. Pat. No. 5,151,350 (Repligen) relates to cloning and expression of the gene coding for a protein A and protein A-like material. The cloning of this gene with its nucleotide sequence characterization enabled in 1982 for the first time to obtain quantities of a protein A-like material and nucleotide sequence for cloning in various host-vector systems.

Since the production of protein A in a recombinant system was accomplished, further genetic manipulations thereof have been suggested. For example, U.S. Pat. No. 5,260,373 (Repligen) describes genetic manipulation of recombinant protein A in order to facilitate the attachment thereof to a support, and more specifically to the coupling thereof via arginine. Further, U.S. Pat. No. 6,399,750 (Pharmacia Biotech AB) describes another recombinant protein A ligand, which has been coupled to a support via cysteine.

However, in order to maintain selectivity and binding capacity, Protein A chromatography matrices of the above-discussed kind need to be cleaned under milder conditions than conventional CIP. In this context, it is understood that the cleaning is closely related to the lifetime of the chromatography matrix. For example, a sensitive matrix may be cleaned with standard CIP, if a reduced performance is acceptable. Thus, efforts have been made to provide chromatography matrices which present the outstanding properties, such as selectivity, of protein A, but which are more resistant to alkaline conditions used for CIP.

Thus, U.S. Pat. No. 6,831,161 (Uhlén et relates to methods of affinity separation using immobilized proteinaceous affinity ligands, wherein one or more asparagine (Asn) residues have been modified to increase alkaline stability. This patent also describes methods of making a stabilized combinatorial protein by modification of Asn residues within a protein molecule to increase stability of the protein in alkaline conditions, and randomization of a protein molecule to modify its binding characteristics, and combinatorial proteins wherein in a step separate from the randomization step, the stability of the protein in alkaline conditions has been increased by modifying one or more of its Asn residues.

Further, WO 03/080655 (Amersham Biosciences) relates to an immunoglobulin-binding protein, wherein at least one asparagine residue has been mutated to an amino acid other than glutamine or aspartic acid. According to this patent application, such more specific mutation confers an increased chemical stability at pH-values of up to about 13-14 compared to the parental molecule. The mutated protein can for example be derived from a protein capable of binding to other regions of the immunoglobulin molecule than the complementarily determining regions (CDR), such as protein A, and preferably from the B-domain of Staphylococcal protein A. The invention also relates to a matrix for affinity separation, which comprises the described mutated immunoglobulin-binding proteins as ligands.

Despite the above-described development t ore alkaline-stable protein A-based chromatography ligands, there is still a need in this field of improved ligands and chromatography matrices for highly specific isolation of antibodies, and of alternative wild type ligand constructions that allow easier manufacture.

One example of such an improved chromatography matrix is described in US 2006/0134805 (Berg et al), which relates to a separation matrix comprised of porous particles to which antibody-binding protein ligands have been immobilised. More specifically, the disclosed chromatography matrix has been optimised in terms of ligand density; gel phase distribution coefficient (Kay); and particle size to provide a matrix especially suitable for high capacity purification of antibodies. The ligands of the disclosed matrix may comprise antibody-binding protein such as Protein A, Protein G and/or Protein L.

SUMMARY OF THE INVENTION

One aspect of the present invention is to provide a novel chromatography ligand, which is capable of withstanding repeated cleaning-in-place cycles. This may be achieved by an affinity ligand which is based on domain C from SpA Domain C, as defined in the appended claims.

Another aspect of the present invention is to provide an economical process of purifying immunoglobulins. This may be achieved by a process which uses an affinity chromatography ligand capable of withstanding repeated cleaning-in-place cycles.

Further aspects and advantages of the invention will appear from the detailed disclosure that follows.

DEFINITIONS

Figure 1:
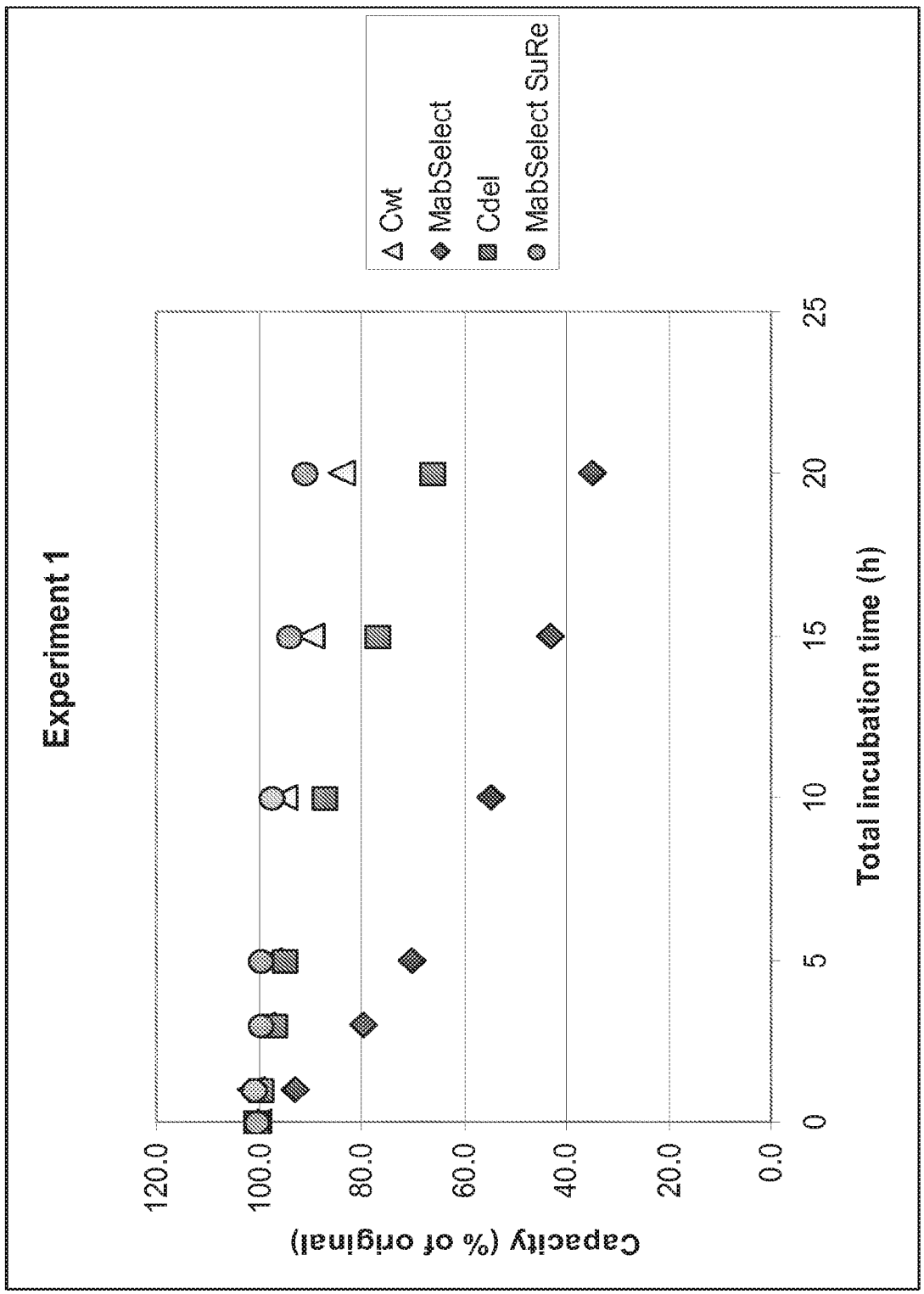
FIG. 1 shows results of testing the alkaline-stability of the ligand according to the invention as compared to other protein-based ligands. The X axis shows the incubation time in hours; while the Y axis shows the capacity that remains after X hours in 0.5M NaOH, as described in Example 1. Mores specifically, the Protein A-containing product MAB-SELECT™ (♦); the more recent Protein A product MAB-SELECT SURE™, marketed as more alkaline-stable (X); Domain C from SpA as defined by SEQ ID NO 1 (Δ); and finally a deleted embodiment of Domain C from SpA as defined by SEQ ID NO 2 (■). As appears from FIG. 1, the Domain C ligand according to the invention shows an alkaline-stability well comparable to the alkaline-stable product MABSELECT SURE™.

The term Domain C or "functional fragments or variants thereof" encompasses fragments or variants of SpA Domain C, which have the property of binding to IgG at the Fc region. The terms "antibody" and "immunoglobulin" are used interchangeably herein, and are understood to include also fusion proteins comprising antibodies and fragments of antibodies.

The term an "Fc-binding protein" means a protein capable of binding to the crystallisable part (Fc) of an antibody and includes e.g. Protein A and Protein G, or any fragment or fusion protein thereof that has maintained said binding property.

The term "Fab fragment" refers to the variable part of an antibody; hence a "Fab-binding ligand" is capable of binding to either full antibodies via Fab-binding; or to antibody fragments which includes the variable parts also known as Fab fragments.

The term "chromatography" is used herein for any kind of separation which utilises the principles of chromatography, and hence includes batch as well as HPLC methods.

The term "affinity chromatography" is used herein for the specific mode of chromatography where the ligand interacts with target via biological affinity in a "lock-key" fashion. Examples of useful interactions in affinity chromatography are e.g. enzyme-substrate interaction, biotin-avidin interaction, antibody-antigen interaction etc.

The term "protein-based" ligands means herein ligands which comprise a peptide or protein; or a part of a peptide or a part of a protein.

The term "isolation" of an antibody is used herein as embracing purification of a specific product antibody from a mixture comprising other proteins, such as other antibodies, and other components; as well as the separation of an antibody from a product liquid, i.e. to remove an undesired antibody.

DETAILED DESCRIPTION OF THE INVENTION

Thus, the present invention relates to a novel chromatography ligand. The chromatography ligand according to the invention, which is protein-based and of the kind known as affinity ligand, comprises all or parts of Domain C from *Staphylococcus* protein A (SpA). In a first aspect, the present invention relates to a chromatography ligand, which ligand comprises one or more Domain C units from *Staphylococcus* protein A (SpA), or a functional fragment or variant thereof in one embodiment, the present chromatography ligand is substantially alkaline-stable. In this context, the term "substantially alkaline-stable" is understood to mean that the ligand is capable of withstanding repeated cleaning-in-place cycles using alkaline wash liquid without loosing its binding capacity. In a specific embodiment, the present invention is a chromatography ligand, comprises Domain C from *Staphylococcus* protein A (SpA), but none of the other domains of SpA.

In an alternative aspect, the present invention relates to a chromatography ligand, which ligand comprises one or more Domain C units from *Staphylococcus* protein A (SpA), or a functional fragment or variant thereof, which chromatography ligand is capable of binding to the Fab part of antibodies, as discussed in more detail below.

As discussed above, Jansson et al have already shown that Domain C can act as a separate immunoglobulin adsorbent, not just as part of Protein A. The present inventors have confirmed that the immunoglobulin binding properties of Domain C are fully satisfactory for the use thereof as a chromatography ligand. As also discussed above, Gülich and others had shown that asparagine and glutamine residues in alkaline conditions is the main reason for loss of protein A activity upon treatment in alkaline solutions, and that asparagine is the most sensitive of the two. Consequently, the Domain C ligand, which contains as many as six asparagine residues, was not be expected to present any substantial alkaline-stability as compared to protein A.

However, as shown in the experimental part below, and in FIG. 1, the present inventors have quite surprisingly shown that the SpA Domain C presents a much improved alkaline-stability compared to a commercially available Protein A product (MABSELECT™, GE Healthcare, Uppsala, Sweden) by incubation in alkaline conditions for durations as long as 20 hours. In fact, the Domain C ligand presents values of alkaline-stability which are similar to those of the product marketed as alkaline-stable (MABSELECT SURE™, GE Healthcare, Uppsala, Sweden), wherein asparagine residues have been mutated to other amino acids.

In addition to this, as discussed above, it has been shown that an especially alkaline-sensitive deamidation rate is highly specific and conformation dependent, and that the shortest deamidation half times have been associated with the sequences—asparagine-glycine- and -asparagine-serine. Quite surprisingly, the Domain C ligand of the invention presents the herein presented advantageous alkaline-stability despite the presence of one asparagine-glycine linkage between residues 28 and 29, using the conventional numbering of the residues of Domain C.

In one embodiment, the ligand according to the invention is able to resist at least 10 hours in 0.5 M NaOH, without deviating more than about 10%, and preferably no more than 5%, from its original immunoglobulin binding capacity, Thus, after 5 hours, it will not deviate more than 10%, preferably 5% from its original binding capacity. In other words, one embodiment of the present invention is a ligand as described above, which after 5 hours incubation in 0.5M NaOH has retained at least 95% of its original binding capacity.

In an advantageous embodiment, the ligand according to the invention is able to resist at least 15 hours in 0.5 M NaOH without loosing more than about 20%, and preferably no more than 10%, of its original immunoglobulin binding capacity. In a more advantageous embodiment, the ligand according to the invention is able to resist at least 20 hours in 0.5 M NaOH without losing more than about 30%, and preferably no more than 15%, of its original immunoglobulin binding capacity. In other words, one embodiment of the present invention is a is a ligand as described above, which after 15 hours incubation in 0.5M NaOH has retained at least 80%, advantageously at least 90% of its original binding capacity.

The skilled person in this field can easily test alkaline-stability by incubating a candidate ligand with sodium hydroxide e.g. as described in the experimental pad, and subsequent testing of the binding capacity by routine chromatography experiments.

As easily realised by the skilled person in this field, a chromatography ligand according to the invention may consist of the wild type SpA Domain C amino acid sequence, as shown in SEQ ID NO 1, herein denoted. Cwt. In an alternative embodiment, the chromatography ligand according to the invention consists of a functional fragment of SpA Domain C, such as the one shown in SEQ TD NO 2, which discloses a sequence herein denoted. Cdel, wherein Asn-Lys-Phc-Asn in positions 3-6 have been deleted as compared to the wild type SpA Domain C sequence. In yet an alternative embodiment, a variant of SpA Domain C is prepared by adding one or more amino acids e.g. to either end of the wild type SpA Domain C amino acid sequence; or by mutation of the wild type SpA Domain C amino acid sequence, provided that such mutation does not substantially interfere with the herein described properties relating to immunoglobulin-binding and alkaline-stability Thus, in a specific embodiment, the chromatography ligand according to the invention comprises SpA Domain C, as shown in SEQ ID NO 1, which in addition comprises the mutation G29A. Alternatively, the chromatography ligand according to this embodiment comprises the deleted SpA Domain C, as shown in SEQ ID NO 2, which consequently comprises said mutation in position 25 (i.e. G25A). As the skilled person will recognise, such addition, mutation or deletion of amino acids as compared to the wild type sequence should preferably not substantially affect the folding pattern of the SpA Domain C ligand.

Thus, in one embodiment, the amino acid sequence of the ligand according to the present invention is the sequence defined by SEQ ID NO 1. In a specific embodiment, the ligand according to the invention comprises at least 60%, advantageously at least 80%, more advantageously at least 90% and most advantageously at least 95%, such as about 98% of the amino acids shown in SEQ ID NO 1. In a specific embodiment, the ligand according to the invention comprises at least 35, advantageously at least 46, more advantageously at least 52 and most advantageously at least 55, such as 57, of the amino acids shown in SEQ ID NO 1.

In an alternative embodiment, the amino acid sequence of the ligand according to the present invention is the sequence defined by SEQ ID NO 2. In a specific embodiment, the ligand according to the invention comprises at least 40%, advantageously at least 77%, more advantageously at least % and most advantageously at least 94%, such as about 98% of the amino acids shown in SEQ ID NO 2. In a specific embodiment, the ligand according to the invention comprises at least 31, advantageously at least 42, more advantageously at least 48 and most advantageously at least 51, such as 53, of the amino acids shown in SEQ NO 2.

As discussed in the section Background above, methods are readily available for coupling of protein ligands via certain amino acids, preferably amino acids that contain nitrogen and/or sulphur atoms, see e.g. U.S. Pat. No. 6,399,750 or 5,084,559. Thus, in one embodiment, the ligand according to the invention further comprises a terminal coupling group, said group preferably comprising one or more nitrogen and/or sulphur atoms. In an advantageous embodiment, the terminal coupling group is comprised of arginine or cysteine. In one embodiment, the coupling group is in the C terminal region.

Further, the present invention also relates to a multimeric chromatography ligand (also denoted a "multimer") comprised of at least two Domain C units, or a functional fragments or variants thereof, as defined above. In one embodiment, this multimer comprises no units originating from SpA. In a specific embodiment, the multimer comprises no other protein-based units. In another embodiment, the multimer comprises no other unit capable of any substantial interaction with a target such as an antibody or a Fab fragment, thus it comprises no other ligand unit. As the skilled person in this field will realise, making a multimer may require adding one or more peptides as linkers between the units. Thus, a multimer limited to containing only Domain C units according to the invention may in addition comprise linkers allowing construction of a multimer wherein each Domain C unit is sufficiently exposed to be able to participate in the binding of target.

In another embodiment, the multimer comprises one or more additional units, which are different from Domain C and preferably protein-based and equally alkaline-stable as Domain C. Thus, in the multimer, the ligand according to the invention may be repeated and/or combined with other units from other sources, such as other proteins. In one embodiment, the multimer is comprised of 2-8 units, such as 4-6 units. In one embodiment, one or more linker sequences are inserted between the multimer units. Such linkers may e.g. be inserted to allow the actual ligand units to maintain their folding pattern. Linkers in this context are well known, and the skilled person can easily decide on suitable amino acids and chain lengths which do not interfere with the herein discussed properties of the ligand. In a specific embodiment, the chromatography ligand according to the invention comprises no other SpA domains than Domain C.

In a second aspect, the present invention relates to a nucleic acid sequence encoding a chromatography ligand as described above. Thus, the invention encompasses all forms of the present nucleic acid sequence such as the RNA and the DNA encoding the ligand. The invention embraces a vector, such as a plasmid, which in addition to the coding sequence comprises the required signal sequences for expression of the ligand according the invention. In one embodiment, the vector comprises nucleic acid encoding a multimeric ligand according to the invention, wherein the separate nucleic acids encoding each unit may have homologous or heterologous DNA sequences. This aspect also embraces an expression system comprising a nucleic acid sequence encoding a ligand according to the invention. The expression system may e.g. be a prokaryotic host cell system, e.g. E. coli which has been modified to express the present ligand. In an alternative embodiment, the expression system is a eukaryotic host cell system, such as a yeast.

As the skilled person in this field will appreciate, the ligand according to the invention may alternatively be produced by protein synthesis methods, wherein the ligand is obtained by an automated process adding amino acids one at a time following a predetermined sequence. In an advantageous embodiment, segments of amino acids amino acid sequences are synthesized and linked to each other to prepare the ligand according to the invention. Such synthesis and linking procedures are well known to the skilled person in this field.

In a third aspect, the present invention relates to a chromatography matrix comprised of ligands as described above coupled to an insoluble carrier. Such a carrier may be one or more particles, such as beads or regular shapes; membranes; filters; capillaries; monoliths; and any other format commonly used in chromatography. Thus, its an advantageous embodiment of the matrix, the carrier is comprised of substantially spherical particles, also known as beads. Suitable particle sizes may be in the diameter range of 5-500 μm, such as 10-100 μm, e.g. 20-80 μm. In an alternative embodiment, the carrier is a membrane. To obtain high adsorption capacities, the carrier is preferably porous, and ligands are then coupled to the external surfaces as well as to the pore surfaces. Thus, in an advantageous embodiment of the matrix according to the invention, the carrier is porous.

The carrier may be made from an organic or inorganic material. In one embodiment, the carrier is prepared from a native polymer, such as cross-linked carbohydrate material, e.g. agarose, agar cellulose, dextran, chitosan, konjac, carrageenan, gellan, alginate etc. The native polymer carriers are easily prepared and optionally cross-linked according to standard methods, such as inverse suspension gelation (S Hjertén: Biochim Biophys Acta 79(2), 393-398 (1964). In an alternative embodiment, the carrier s prepared from synthetic polymer or copolymer, such as cross-linked synthetic polymers, e.g. styrene or styrene derivatives, divinylbenzene, acrylamides, acrylate esters, methacrylate esters, vinyl esters, vinyl amides etc. Such synthetic polymer carriers are easily prepared and optionally cross-linked according to standard methods, see e.g. "Styrene based polymer supports developed by suspension polymerization" (R Arshady: Chimica e L'Industria 70(9), 70-75 (1988)). Native or synthetic polymer carriers are also available from commercial sources, such as GE Healthcare Bio-Sciences AB, Uppsala, Sweden, for example in the form of porous particles. In yet an alternative embodiment, the carrier is prepared from an inorganic polymer, such as silica. Inorganic porous and non-porous carriers are well known in this field and easily prepared according to standard methods.

In a fourth aspect, the present invention relates to a method of preparing a chromatography matrix, which method comprises providing ligands as described above; and coupling of said ligands to a carrier. In an advantageous embodiment, the coupling is carried out via a nitrogen or sulphur atom of the ligand. In brief, the ligands may be coupled to the carrier directly; or indirectly via a spacer element to provide an appropriate distance between the carrier surface and the ligand. Methods for immobilisation of protein ligands to porous or non-porous surfaces are well known in this field; see e.g. the above-discussed U.S. Pat. No. 6,399,750.

In a fifth aspect, the present invention relates to a process of isolating one or more target compounds, which process comprises contacting a liquid comprising said compound(s) with a chromatography matrix; allowing said compound(s) to adsorb to ligands present on the matrix, wherein said ligands consists of one or more Staphylococcus protein A (SpA) Domain C, and/or functional fragments or variants thereof; and, optionally, eluting said compound(s) by the passing across said matrix of a liquid that releases compound(s) from ligands. Thus, in this embodiment, the ligands comprise no other. SpA-derived domain than Domain C, or a functional fragment or variant thereof. In an alternative embodiment, said ligands are multimers comprising two or more SpA Domain C units, or functional fragments or variants thereof.

In an advantageous embodiment, the ligands are the ligands described above. The target compound(s) may be any organic compound, bio molecule or other biological material, such as proteins, e.g. antibodies; peptides; cells, such as eukaryotic and prokaryotic cells; nucleic acids, such as DNA, e.g. plasmids, and RNA; virus; etc. In an advantageous embodiment, the target compound(s) is one or more monoclonal or polyclonal antibodies, such as IgA, IgD, IgE, IgG, and IgM. In one embodiment, the target compound is a fragment of an antibody, such as a Fab fragment. In yet another embodiment, the target compound is a fusion protein wherein at least one part is an antibody or an antibody fragment.

In one embodiment, the chromatography matrix is a disposable product, and elution will then not be required if the purpose of the process is to remove the target compound such as the antibody from a product liquid. This embodiment may e.g. be for the removal of an undesired antibody from a liquid, such as a medical liquid or a liquid wherein many antibodies are produced, such as milk from a recombinant animal.

In an alternative embodiment, when the adsorbed compound is the desired product, the elution step is included in the process. To obtain the most suitable conditions for adsorption, a liquid sample is combined with a suitable buffer or other liquid such as water to provide the mobile phase. The present method is advantageously run under conditions conventional for affinity chromatography, and especially for protein A chromatography, as is well known in this field.

In a sixth aspect, the present invention relates to the use Domain C of SpA, or a functional fragment or variant thereof, as alkaline-stable immunoglobulin adsorbent. In this context, "alkaline-stable" is understood to mean that the adsorbent alkaline-stability is not lower than about 10%, such as about 5%, below that of a commercial products marketed as being alkaline-stable, such as MABSELECT SURE™ (GE Healthcare Bio-Sciences AB, Uppsala, Sweden) during the first 5 hours of incubation in 0.5M NaOH. In an advantageous embodiment, the adsorbent is a ligand as described above. As said MABSELECT SURE™ should present a minimal deterioration after such time and conditions, the antibody binding capacity of the adsorbent should not be lower than about 10%, such as about 5%, below its original binding capacity after such time and conditions. In this context, the term "original" refers to its capacity before any alkaline regeneration, and the comparisons are carried out as side-by-side experiments using a procedure of the herein disclosed kind.

In one embodiment, the use according to the invention comprises a process as described above, wherein the antibodies are eluted from the matrix and which is carried out at least once, such as 2-300 times, optionally with washing steps between; alkaline regeneration of the matrix; and finally repeating said process of isolating antibodies, Washing may be carried out with a suitable buffer, such as the buffer used to equilibrate the column. In an advantageous embodiment, the regeneration is carried out by incubation with 0.5 M NaOH.

The present invention also embraces a method of purifying one or more target compounds, as discussed above, which method comprises one or more chromatography steps in addition to the purification using the chromatography matrix according to the invention. The method according to this aspect may e.g. comprise s first chromatography step using the present matrix; an intermediate chromatography step using either ion exchange or hydrophobic interaction chromatography (HIC); and finally a polishing step using ion exchange, HIC or reverse phase chromatography. In a specific embodiment, this process comprises a step preceding the chromatography matrix having Domain C ligands as described herein. Such a preceding step may e.g. be a conventional filtration, sedimentation, flocculation or other step to remove cell debris and other undesired components.

In an alternative embodiment, the use according to the invention is an analytical or diagnostic use, such as an immunoassay.

EXAMPLES

The present examples are provided as illustrative purposes only, and should not be construed as limiting the present invention as defined in the appended claims.

Example 1: Column Study of the Alkaline Stability of Four Protein A-Derived Ligands In this example, the alkaline stability of four chromatography matrices, two of which were comparative and two of which were according to the invention, were tested through a series of chromatographic runs:
MABSELEC™ and MABSELECT SURE™ (both comparative products comprising protein-based ligands, GE Healthcare Bio-Sciences, Uppsala, Sweden), and
Cwt (wild type Domain C from SpA, as defined in SEQ NO. 1), and Cdel (deleted wild type Domain C from SpA, as defined in SEQ ID NO. 2).

The IgG-binding capacity was measured initially and after incubation steps in 0.5 M NaOH. The incubation times varied from one to five hours, with an accumulated incubation time of 20 hours.

The ligands according to the invention were immobilized on agarose particles according to standard procedure and packed in columns (GE Healthcare). Two of the matrices, MABSELECT™ and MABSELECT SURE™, are commercial products manufactured by GE Healthcare marketed for the purification of monoclonal antibodies. The ligands of both products are based on the IgG binding *Staphylococcus aureus* Protein A. The MABSELECT™ ligand basically is recombinant Protein A, which consists of five homologous domains (E, D, A, B, C). By comparison, the MABSELECT SURE™ ligand consists of four domains which originate from the domain B analogue "Z", which in turn has been stabilized against high by protein engineering methods. As a result, MABSELECT SURE™ tolerates cleaning-in-place (CIP) conditions of up to 0.5 M NaOH. Both the MABSELECT™ and MABSELECT SURE™ ligands are coupled to agarose particles.

The ligands Cwt and Cdel were constructed as tetramers of identical domains with a C-terminal cysteine residue for coupling to a matrix according to standard procedure.

Materials & Methods
Target Compound

10×10 ml injection liquid, solution, GAMMANORM® 165 mg/ml (Octapharma no. 00 86 64), human normal immunoglobulin, for subcutane infusion or intramuscular injection, was used as the target compound in the chromatography experiments.

Chromatography Columns

Ligand coupling and column packing was carried out as outlined in Table 1 below:

TABLE 1

Columns used in Experiment 1

| Ligand/Matrix | Column ID | Column no. | Batch | Date | Column volume (ml) |
|---|---|---|---|---|---|
| MABSELECT SURE ™ | 9 | 4 | U669082 | 2006 Mar. 10 | 2.08 |
| Cwt | 11 | 2 | U1555055A | 2006 Mar. 10 | 2.02 |
| MABSELECT ™ | 1 | 7 | U1555045A | 2006 Mar. 10 | 2.12 |
| Cdel | 13 | 2 | U1555059A | 2006 Mar. 03 | 2.06 |

"Column ID" refers to a unique number given to each column. These numbers were included in the chromatography methods and can be found in the logbook of the result files. For example, the first column in table 1 was called "MABSELECT SURE™ U669082 Column 4 20060310 (9)". "Column no." is the packing number, i.e. columns packed with the same batch of matrix received different Column nos. upon packing. The column volume was estimated by measuring the bed height.

Buffers and Solutions
Buffer A: 50 mM Sodium phosphate, 0.15 NI NaCl, pH 7.2
Buffer B: 50 mM Citric acid, 0.15 M NaCl, pH 2.5
Instruments and Laboratory Equipment
Chromatography system: ÄKTA EXPLORER™ 10 (GE Healthcare
Column hardware: TRICORN™ Wm 5/100 GL (GE Healthcare)
Vacuum degasser: CT 2003-2, 2 channel degasser, ChromTech AB
Spectrophotometer: NANODROP™ ND-1000 Spectrophotometer, NanoDrop Technologies
Centrifuge: Beckman Coulter AVANTI® J-20 XPI with JLA 8.1000 rotor
pH meter (Buffer A): Beckman Φ 360 pH/Temp/mV Meter
pH meter (Buffer B): Laboratory pH Meter CG 842, SCHOTT
Helium: AGA Gas AB, 10 1 H 20577708, Instrument
Filter for buffer and sample: 75 mm Bottle Top Filter 500 ml, 0.2 μm pore size, Nalgene
Filter for 0.5 M NaOH: 75 mm Bottle Top Filter—500 ml, 0.45 μm pore size, Nalgene
Software
ÄKTA EXPLORER™ 10 was controlled by UNICORN™ 5.01 (GE Healthcare). Apart from controlling the system during the chromatography runs, UNICORN™ was used for method programming and evaluation of the results.
Buffer Preparation Buffer A: Sodium dihydrogen phosphate and NaCl were dissolved in water, A pH meter was calibrated using pH 4, pH 7 and pH 10 standard buffers. pH was monitored adding NaOH(aq) to the buffer until pH reached 7.2. The buffer was filtered and degassed with helium prior use.

Buffer B: Citric acid and NaCl were dissolved in water. A pH meter was calibrated, using pH 7 and pH 2 standard buffers. pH was monitored while adding NaOH(aq) to the buffer until pH reached 2.5. The buffer was filtered and degassed with helium prior use.

Preparation of 0.5 M NaOH

NaOH(s) was dissolved in water to 0.5 M. The solution was filtered and degassed with helium prior use.

Sample Preparation
Experiment 1

30 ml Gammanorm (165 mg/ml) was diluted to 1 mg/ml with 4950 ml Buffer A. The sample was filtered through 0.2 urn into a sterile 5 litre bottle.

Three 280 nm absorbance measurements were performed on the sample using NANODROP™ spectrophotometer: 1.2573 AU, 1.2432 AU and 1.2101 AU. Mean absorbance: 1.2369 AU.

The absorbance at 280 nm was also measured on ÄKTA EXPLORER™ 10. The sample was pumped with the system pump through the system in bypass mode. A 10 min UV cell was used and the flow rate was 0.83 ml/min. The absorbance at 280 nm was 1510 mAU. This value was used as a reference when making capacity calculations.

Method Description

Normally, a CIP cycle for MABSELECT SURE™ involves 10-15 minutes contact time of the CIP solution ally 0.1-0.5 M NaOH). To reduce the amount of CIP cycles in this study, longer contact times were used. The columns were incubated for 1, 2 and 5 hour intervals, with a total contact time of 20 hours. This corresponds to 80 to 120 cycles with 10-15 minutes contact time.

Prior to the CIP incubations two initial capacity measurements were performed per column. After the capacity measurements the columns were incubated in 0.5 M NaOH. After each CIP incubation, one capacity measurement per column was carried out.

Schematically, the experiment was designed as follows:
Two initial capacity measurements per column.
CIP incubation, 1 hour.
One capacity measurement per column.
CIP incubation, 2 hour.
One capacity measurement per column.
CIP incubation, 2 hour.
One capacity measurement per column.
CIP incubation, 5 hour.
One capacity measurement per column.
CIP incubation, 5 hour.
One capacity measurement per column.
CIP incubation, 5 hour, One capacity measurement per column.

System Setup:

The experiments were carried out in room temperature. However, the sample was kept on ice to avoid microbial growth. To avoid the formation of air bubbles when the cold sample was heated to room temperature, a degasser was connected between the sample and the pump. The ÄKTA EXPLORER™ 10 was equipped with a 10 mm UV cell for JV detection.

Both buffer and sample was pumped through the system pumps. Following inlets were used:

Sample: B pump (inlet B1)
Buffer A: A pump (inlet A11)
Buffer B: A pump (inlet A12)
0.5 M NaOH: A pump (inlet A13)

Capacity Measurement, Detailed Description

Prior to a capacity measurement (consisting of one capacity measurement per column) sample was pumped in bypass mode, i.e. no column used. The purpose of this was to get "fresh" sample to each capacity measurement and to avoid loading the first volume of sample that remained in tubes and the pump in room temperature during the CIP incubations, onto the first column.

The capacity measurement method for each column consisted of following parts:

Equilibration of the column with 5 column volumes (CV) Buffer A.

Sample loading. Dynamic binding capacity is determined by loading a sample onto a column packed with the chromatography medium of interest. When the medium becomes more and more saturated with sample, the level of absorbance at 280 nm will increase due to unbound sample passing through the column. In this method, the sample was loaded onto the column until the $UV_{280nm}$ curve reached 15% of the 280 nm absorbance of the sample.

Wash out unbound sample. The column was washed with Buffer A until the $UV_{280nm}$ curve dropped below 10% of the 280 nm absorbance of the sample Elution. Bound material was eluted with 10 CV of Buffer B.

Reequilibration with 5 CV Buffer A.

The flow rate of sample loading was 0.83 ml/min.

CIP Incubation

After each capacity measurement, except for the first of the two initial measurements, a CIP incubation was carried out. In the CIP incubation method, 3 CV of 0.5 M NaOH was pumped through each column at a flow rate of 0.83 ml/min. After this the system was set to pause. The length of the pause depended on the length of the CIP incubation time, i.e. 1 h, 2 h or 5 h. However, the time required for the system to pump NaOH through the columns was subtracted from the pause time. After a CIP incubation 3 CV of Buffer A was pumped through each column at a flow rate of 0.83 ml/min to remove the NaOH. By this procedure, all columns were exposed the same amount of time to NaOH. One more wash cycle with 3 CV Buffer A was finally carried out.

Evaluation of Chromatographic Results

Capacity was determined by measuring the volume of sample applied onto a column until the absorbance at 280 nm reached 10% of the sample absorbance. The dead volumes, i.e. the column volume, mixer and tubing from the pump to the UV cell, were subtracted from this volume. The delay volume without column was determined to 1.02 ml. The capacity values were plotted against the accumulated CIP incubation times. Relative capacity values were achieved by dividing the capacity values after the CIP cycles with the mean of the start capacity values. The relative capacity values were used for easier comparisons between the different matrices.

TABLE 2

Results Experiment 1 -
Capacity (mg Gammanorm/ml chromatography matrix(gel))

| | MABSELECT SURE ™ | Cwt | MABSELECT ™ | Cdel |
|---|---|---|---|---|
| Start Capacity 1 | 28.38 | 27.43 | 28.98 | 30.86 |
| Start Capacity 2 | 28.13 | 27.40 | 28.98 | 30.95 |
| Capacity after 1 h | 29.32 | 27.79 | 26.98 | 30.75 |
| Capacity after 3 h | 28.42 | 27.26 | 23.08 | 29.88 |
| Capacity after 5 h | 28.25 | 26.94 | 20.30 | 29.25 |
| Capacity after 10 h | 27.88 | 26.07 | 15.79 | 26.87 |
| Capacity after 15 h | 27.01 | 24.65 | 12.52 | 23.70 |
| Capacity after 20 h | 25.93 | 23.02 | 10.14 | 20.35 |

Experiment 2: Test of Fab-Binding

The Fab-binding ability of the different chromatography media was evaluated, in a 96-well filter plate assay. Liquids and chromatography media were mixed on a plate vortex instrument for 1 minute. The bottom of the wells consisted of a filter which retained liquids and the particles of the chromatography media. When subjected to centrifugation, the liquids passed through the filter and were collected in a separate 96-well collection UV-plate attached to the bottom of the filter plate. The absorbance at 280 nm of the collected liquid was measured in a plate reader and used for detection and estimation of Fab. The liquids from different steps, e g washing, elution, were collected in different plates and measured separately, to be able to measure the amount of Fab in individual fractions.

10% slurry was prepared of each chromatography medium.

The filter plates were loaded with 200 µl slurry/well, i.e. 20 µl medium/well.

Equilibration—5×200 µl wash in PBS

Sample incubation—100 µl of human polyclonal Fab/Kappa, IgG fragment (Bethyl) in PBS, 15 minutes Wash—5×100 µl PBS Elution—3×100 µl 0.1 M glycine, pH 3.0

CIP—2×10 min with 0.5 M NaOH

Analyze plates with liquids UV @ 280 nm

Figure 2:
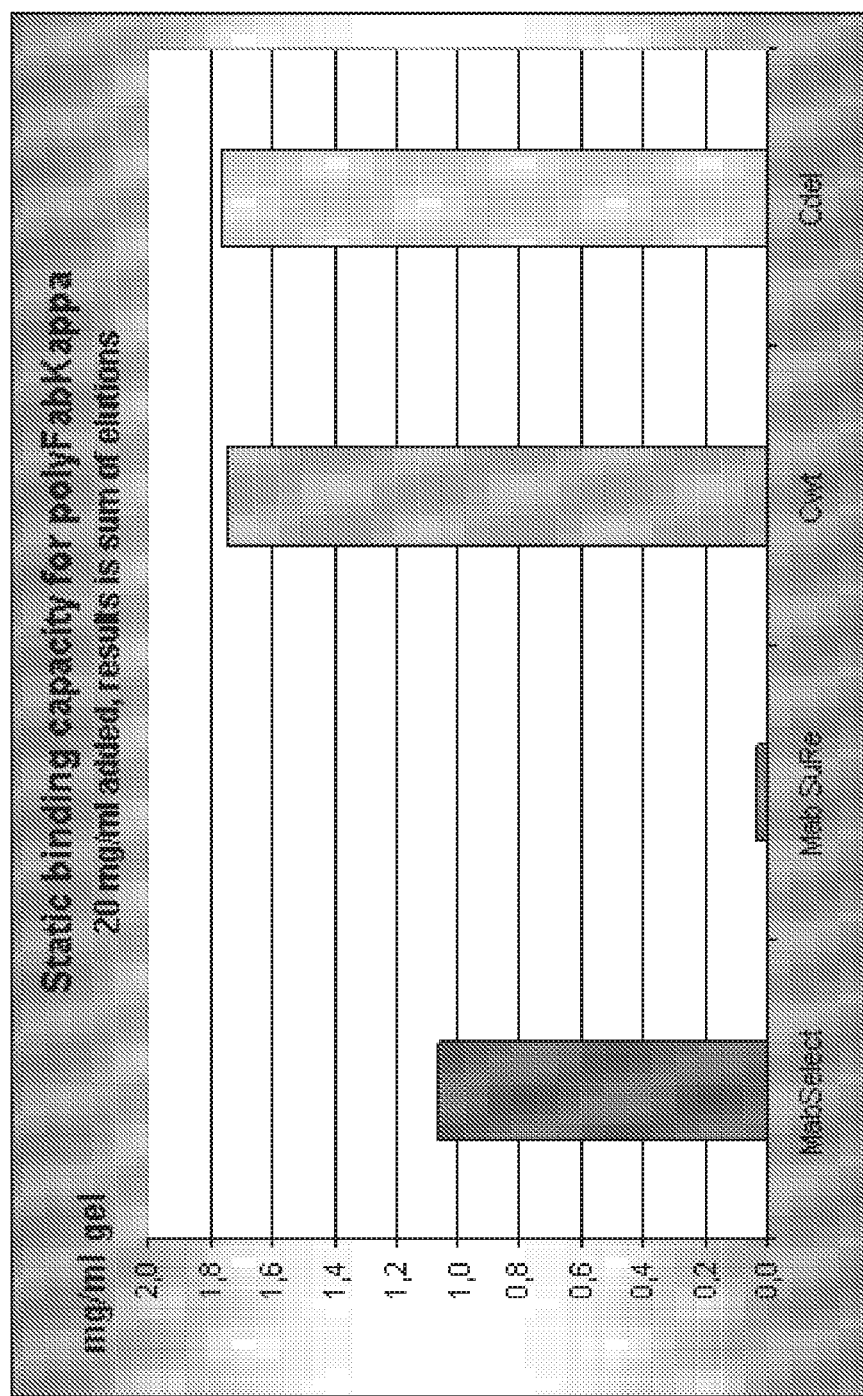
FIG. 2 shows the results of testing the Fab-binding properties of the ligand according to the invention, as compared to other protein-based ligands. As appears from this figure, a chromatography ligand comprising Domain C from SpA (Cwt and Cdel) present a much higher levels of Fab-binding than the other tested ligands.

The results of experiment 2 are presented in FIG. 2.

The above examples illustrate specific aspects of the present invention and are not in-tended to limit the scope thereof in any respect and should not be so construed. Those skilled in the art having the benefit of the teachings of the present invention as set forth above, can effect numerous modifications thereto. These modifications are to be construed as being encompassed within the scope of the present invention as set forth in the appended claims.

What is claimed is:

1. A separation matrix comprising a plurality of chromatography ligands coupled to a solid support,
wherein the ligand comprises one or more mutated Domain C of Staphylococcus protein A (SpA) which has a sequence that is at least 77% identical to the amino acid sequence shown in SEQ ID NO:2.

2. The separation matrix of claim 1, wherein the ligand is capable of binding to the Fab part of an antibody.

3. The separation matrix of claim 1, wherein the ligand comprises one or more mutated Domain C of Staphylococcus protein A (SpA) which has a sequence that is at least 98% identical to the amino acid sequence shown in SEQ ID NO: 2.

4. The separation matrix of claim 1, wherein the one or more mutated Domain C of Staphylococcus protein A (SpA) comprises SEQ ID NO: 2 with mutation G25A.

5. The separation matrix of claim 1, wherein at least one asparagine in the sequence of the ligand is replaced with an amino acid other than glutamine or aspartic acid.

6. The separation matrix of claim 1, wherein the ligand comprises a terminal coupling group comprising at least one nitrogen and/or sulphur atom(s).

7. The separation matrix of claim 6, wherein the terminal group comprises arginine or cysteine.

8. The separation matrix of claim 1, wherein the ligand is coupled to the solid support via thioether bonds.

9. The separation matrix of claim 1, wherein the ligand is multimeric and comprises at least two Domain C mutants.

10. The separation matrix of claim 9, wherein the multimeric ligand comprises one or more other alkaline-stable protein-based units.

11. The separation matrix of claim 9, wherein the multimeric ligand comprises 2-8 Domain C units, optionally coupled via linker segments.

12. The separation matrix of claim 1, wherein the solid support is a polysaccharide.

13. The separation matrix of claim 1, wherein the solid support is comprised of substantially spherical particles.

14. The separation matrix of claim 1, wherein the solid support is porous.

* * * * *

UNITED STATES PATENT AND TRADEMARK OFFICE
CERTIFICATE OF CORRECTION

| | | |
|---|---|---|
| PATENT NO. | : 11,517,879 B2 | |
| APPLICATION NO. | : 17/107600 | |
| DATED | : December 6, 2022 | |
| INVENTOR(S) | : Martin Hall et al. | |

It is certified that error appears in the above-identified patent and that said Letters Patent is hereby corrected as shown below:

On the Title Page

In the terminal disclaimer dated January 3, 2022, replace prior patent number "10123765" with --10213765--. On Page 1 of DIST.E.FILE, the patent number is under the Owner/Percent section.

In the Claims

In Claim 1, Line 5, replace "77%" with --94%--.

Signed and Sealed this
Nineteenth Day of September, 2023

Katherine Kelly Vidal
*Director of the United States Patent and Trademark Office*